United States Patent [19]
Sugano

[11] Patent Number: 5,215,377
[45] Date of Patent: Jun. 1, 1993

[54] THERMOGRAVIMETRIC APPARATUS

[75] Inventor: Yoshiharu Sugano, Tokyo, Japan

[73] Assignee: Seiko Instruments Inc., Tokyo, Japan

[21] Appl. No.: 799,833

[22] Filed: Nov. 27, 1991

[30] Foreign Application Priority Data

Nov. 29, 1990 [JP] Japan .................... 2-339879

[51] Int. Cl.$^5$ ............................ G01N 25/00
[52] U.S. Cl. ...................... 374/14; 414/225; 901/7
[58] Field of Search .......... 374/14; 901/7, 17; 414/225, 226, 744.1, 744.8

[56] References Cited

U.S. PATENT DOCUMENTS

| | | | |
|---|---|---|---|
| 3,045,472 | 7/1962 | Paulik et al. | 374/14 |
| 3,760,956 | 9/1973 | Burch | 901/7 |
| 4,556,362 | 12/1985 | Bahnck et al. | 414/225 |
| 4,606,649 | 8/1986 | Mikhail | 374/14 |
| 4,782,567 | 11/1988 | Kanaya et al. | 414/225 |

FOREIGN PATENT DOCUMENTS 2203244 8/1990 Japan ...................... 374/14

Primary Examiner—William A. Cuchlinski, Jr.
Assistant Examiner—G. Bradley Bennett
Attorney, Agent, or Firm—Spensley Horn Jubas and Lubitz

[57] ABSTRACT

The efficiency and measuring accuracy of thermogravimetry are improved by performing sample conveyance and thermogravimetry alternately, interruptedly and automatically by the provision of apparatus composed of a thermobalance having a holder for holding a sample container and a heating oven, a sample container tray initially carrying the sample container, and an auto-sampler for automatically conveying the sample container from the sample container tray to the holder and vice versa, the devices being combined to effect conveyance of the sample container from the sample container tray to the holder automatically and continuously and thus to improve the measuring accuracy.

12 Claims, 4 Drawing Sheets

THERMOGRAVIMETRIC APPARATUS

BACKGROUND OF THE INVENTION

The present invention relates to a thermogravimetric apparatus for measuring the dependency of the weight of a sample upon temperature.

Generally speaking, existing thermal analyses are divided into thermogravimetry, differential thermal analysis and differential scanning calorimetry using a thermobalance. Of these, differential thermal analysis has been used for many years, but its measuring accuracy and performance have remarkably improved in recent years with progress in instrumentation.

Moreover, analysis per se has a wide field of application so that it is widely used for analyzing the properties of materials, for investigating and developing new materials, and further for quality control. Partially automated apparatus exists, but no thermobalance for thermogravimetry has ever been automated and made continuous, so that its measurements are manually performed. In recent years, therefore, continuous measurement has been desired in thermal analyzers.

In the case of thermogravimetry using a thermobalance, one sample container is replaced by another for each measurement. Since the sample containers take different positions for the measurements, manual methods are inefficient for making measurements.

SUMMARY OF THE INVENTION

The present invention has as an object to provide thermogravimetric apparatus which is automated and made continuous by equipping such apparatus with an auto-sampler.

According to a major feature of the present invention, there is provided a thermogravimetric apparatus comprising: a holder for holding a sample container; a thermobalance having a heating oven with a temperature controller; a tray for holding the sample container; and auto-sampled means capable of conveying the sample container from the tray to the holder and vice versa, whereby the sample container is fed and discharged between the tray and the holder so that thermogravimetry may be accomplished successively and interruptedly.

A first one of a plurality of sample containers arranged on a tray is gripped and conveyed onto a holder by an auto-sampler. A heating oven is disposed to cover the sample holder to perform the thermogravimetry. After this, the heating oven is moved away, and the sample container held on the sample holder is returned to the tray by the auto-sampler. By repeating a series of similar operations, the thermogravimetry of the samples is accomplished automatically and continuously to enhance the measuring efficiency. Moreover, the conveyance to a fixed position can be effected by the auto-sampler to reduce positioning variations to thereby enhance the measuring accuracy.

DESCRIPTION OF THE PREFERRED EMBODIMENTS

The present invention will be described in detail below with reference to the accompanying drawings.

Figure 1:
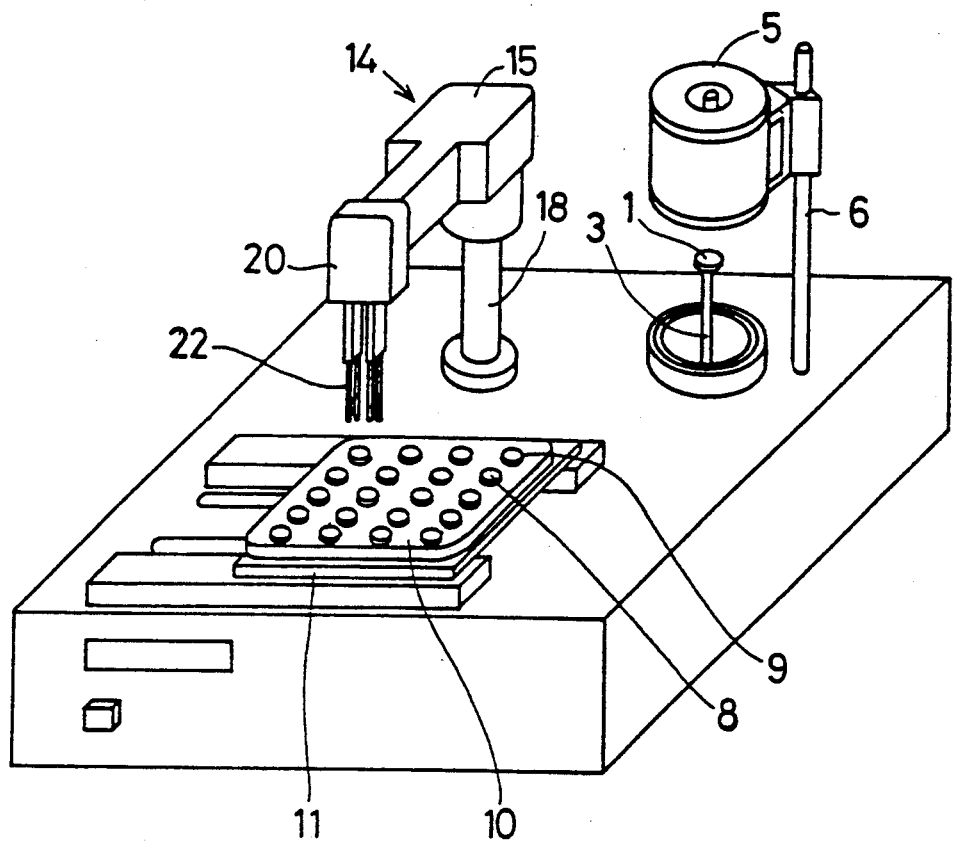
FIG. 1 is a perspective view showing a thermogravimetric apparatus according to one embodiment of the present invention.
Figure 2:
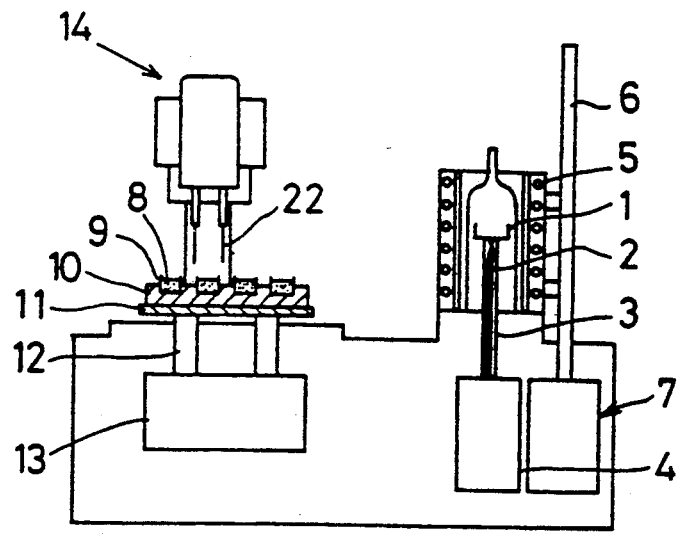
FIG. 2 is an elevational cross-sectional view showing a major structural portion of the apparatus of FIG. 1.

FIG. 1 is a perspective view of an apparatus for showing the whole structure of the present invention, and FIG. 2 is a sectional view showing the structure of a heating oven transfer mechanism forming a major portion of the apparatus of FIG. 1.

First of all, the major portion of the measuring apparatus of the present invention will be described in the following.

In FIGS. 1 and 2, reference numeral 1 designates a holder which is molded of pure platinum, sintered alumina or the like for holding a sample container thereon. Holder 1 is fixed to one end of a balance beam 3 which is molded of a sintered alumina tube. The other end of balance beam 3 is connected to a shaft (not shown) of a balance unit 4. In the tube of the balance beam 3, there is fitted a thermocouple 2 which has its hot junction end welded fixedly to the bottom of the aforementioned holder 1. A heating oven 5 is connected through a connecting rod 6 to its transfer mechanism 7 having a motor therein, so that oven 5 can be moved vertically and pivotably, about a vertical axis, by the transfer mechanism 7.

Reference numeral 10 identifies a tray which has a flat plate which is constructed to have a uniform array of circular grooves carrying, in the order of measurement, cup-shaped sample containers 9 containing samples 8. A tray bed 11 for carrying tray 10 is connected through connecting rods 12 to a tray conveyor mechanism 13 so that tray 10 can be reciprocated back and forth and to the right and left, i.e. in two mutually perpendicular directions in a horizontal plane.

Figure 3:
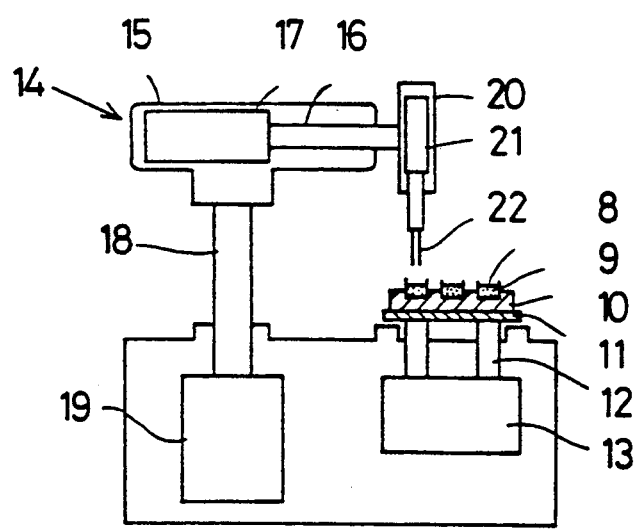
FIG. 3 is an elevational cross-sectional view showing the auto-sampler unit of FIG. 1 schematically.

Now, the auto-sampler means of the apparatus of FIGS. 1 and 2 will be described. As shown in FIG. 3, the auto-sampler 14 is composed of: a robot arm unit 15, to be described later herein; a drive shaft 18 for driving arm unit 15; a drive mechanism 19 for driving arm unit 15 vertically and pivotably about a vertical axis; and a finger moving unit 20.

Robot arm unit 15 is equipped therein with a robot arm 16 and an arm drive mechanism 17 for reciprocating the robot arm 16. Robot arm unit 15 is supported by the drive shaft 18, which in turn is connected to the drive mechanism 19 so that unit 15 can be moved pivotably and vertically by the drive mechanism 19.

At the front end of robot arm 16, there is fixed the finger moving unit 20, which is equipped with a finger unit 22 and a finger drive mechanism 21. The finger unit 22 is composed of a pair of fingers, which can be opened or closed by the finger drive mechanism 21, employing an eccentric cam, which is well known. It will be appreciated that mechanism 21 could be constructed to move unit 22 vertically.

Next, the operation of the embodiment of FIGS. 1-3 will be described. At first, the sample containers 9 containing the samples 8 to be measured are arranged in advance on the tray 10 in the desired measuring order. When the apparatus is actuated, the tray 10 is moved horizontally to a predetermined first position by the tray moving mechanism 13.

Next, robot arm 16 is extended by arm drive mechanism 17, and the fingers 17 of finger unit 22 are then moved onto the first sample container 9 by operation of drive mechanism 19. When finger drive mechanism 21 is actuated, the leading end portions of the fingers of finger unit 22 grip and hold a sample container 9. Drive mechanism 19 is actuated to move the sample container 9 upwardly by the lifting motion of the drive shaft 18 and then toward holder 1 by the pivoting motion of shaft 18. In this position, robot arm 16 is moved downward until it is stopped at a predetermined position. In this position, the fingers of finger unit 22 are opened again to place the sample container 9 on the aforementioned sample holder 1, thus ending the series of conveying operations. After this, the heating oven 5 is moved downward by the heating oven transfer mechanism 7 to cover the outer periphery of the sample, and a subsequent measurement is started.

Next, the sequence of movements associated with a measuring operation will be described. When sample 8 is heated by heating oven 5, its temperature is detected by thermocouple 2 in holder 1, and the weight change of sample 8 is measured by balance 4. After the measurements, the heating oven 5 is transferred to a location above sample holder 1. Then, by operations similar to the aforementioned ones, finger unit 22 is moved to a location above sample holder 1 and is closed to grip the sample container 9 on holder 1 and to then convey sample holder 9 backward, pivotally and downward to the original position on the tray 10.

The next sample container 9 is likewise sequentially conveyed from sample container tray 10 onto sample holder 1 so that it is measured.

Now there will be described another embodiment of the thermogravimetric apparatus having an auto-sampler, when the thermobalance has a structure of horizontally differential type.

Figure 4:
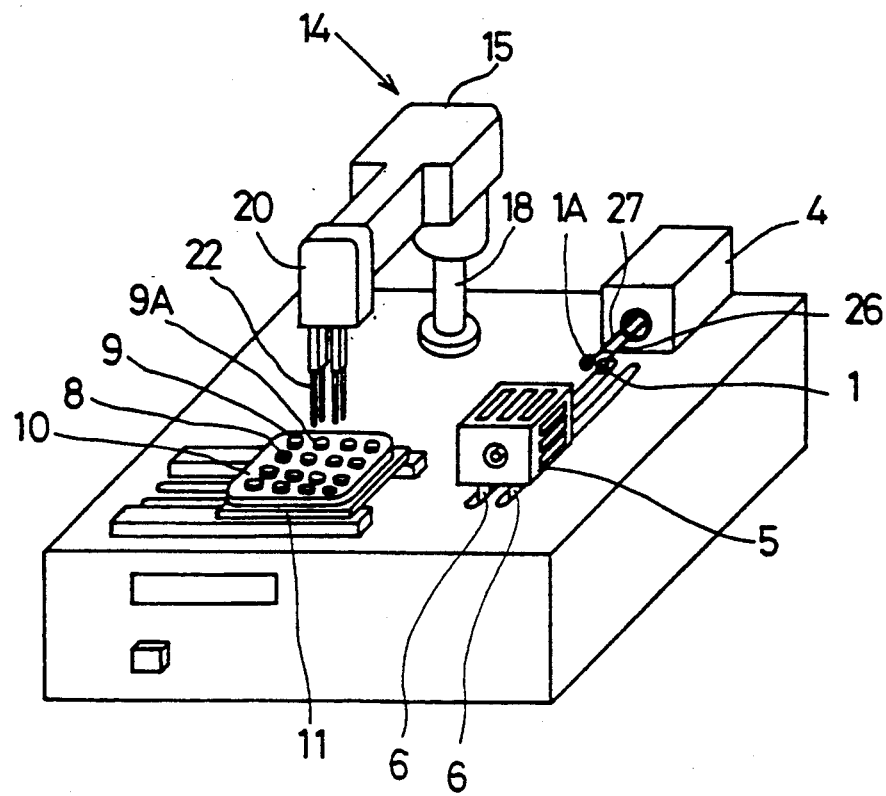
FIG. 4 is a perspective view showing a horizontal differential thermogravimetric apparatus according to another embodiment of the present invention.
Figure 5:
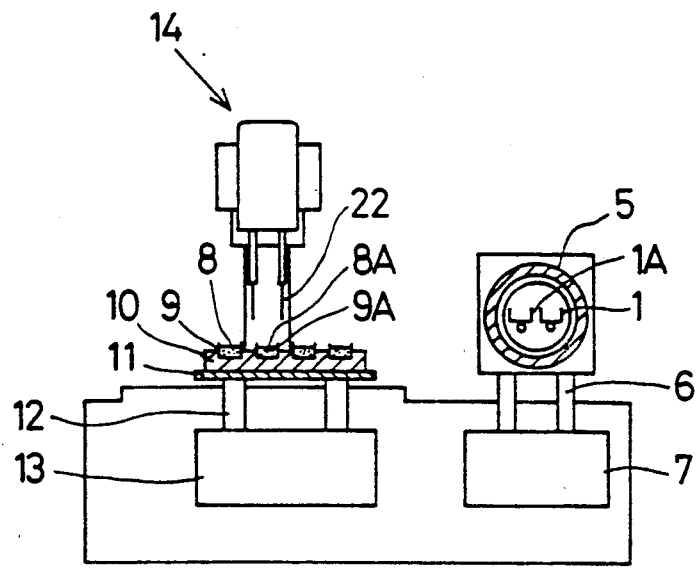
FIG. 5 is an elevational cross-sectional view showing the sample holder, the sample container tray and their environment for the embodiment of FIG. 4.

FIG. 4 is a perspective view showing a horizontal differential type thermogravimetric apparatus according to another embodiment, and FIG. 5 is a section showing an essential portion of the apparatus of FIG. 4. The sample holder 1 is a holder for holding a sample container containing a sample to be measured. A reference holder 1A is provided for holding a sample container containing a reference sample (e.g., alumina powder) which will not be subjected to thermal transformation. The sample holder 1 is fixed to one end of a sample side balance beam 26 which is formed into a tubular shape. On the other hand, the reference holder 1A is fixed to one end of a reference side balance beam 27 which is also formed into a tubular shape. The other ends of those beams are individually connected to the balance unit 4. The heating oven 5 has its lower portion connected through the connecting rods 6 to a heating oven transfer mechanism 7 so that it can be reciprocated horizontally. Oven 5 is arranged to surround sample holder 1 and reference holder 1A. In other words, the present embodiment is constructed differently from the foregoing embodiment 1 in that the heating oven 5 is moved horizontally. Moreover, the remaining components are similar to those of the first-described embodiment so that their descriptions will be omitted.

In the operations of the embodiment of FIGS. 4 and 5, at first, a sample container 9 containing a sample 8 to be measured and another sample container 9A containing a reference sample are separately arranged in the measuring order on the tray 10. When the apparatus is operated, operations similar to those of the first embodiment are performed. Specifically, at first, tray 10 is moved by tray moving mechanism 13 to a predetermined first position on tray bed 11, and sample container 9 is placed on sample holder 1 by operations similar to those previously described by auto-sampler 14. Next, tray 10 is moved to a predetermined second position by tray moving mechanism 13 so that the sample container 9A containing the reference sample is placed on the reference holder 1A by the conveying action of auto-sampler 14. After this, heating oven 5 is moved horizontally to surround the aforementioned sample holder 1 and reference holder 1A, and the measurements are started. After measurements have been completed, the operations previously described are reversed to return the measured sample container 9 and the reference sample container 9A onto tray 10 by the action of auto-sampler 14.

By repeating the series of operations thus far schematically described, the horizontal differential type thermogravimetric apparatus can exchange both the sample container and the reference container and can perform the thermogravimetry on successive sample/reference sample pairs automatically and sequentially.

As has been described hereinbefore, according to the present invention, the thermogravimetry of a variety of many samples can be performed automatically and continuously to improve the measuring efficiency. Since, moreover, the sample container can be placed in a fixed position on the sample holder by the auto-sampler, positional deviations, or variations, can be reduced, in contrast to the prior art, so that the measurement deviations can be minimized to improve the measuring accuracy.

This application relates to subject matter disclosed in Japanese Application number 2-339879, filed on Nov. 29, 1990, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A thermogravimetric apparatus comprising: a thermobalance having a sample holder mounted at a location which is horizontally fixed for holding a sample container which contains a sample and a heating oven with an oven temperature controller; a tray for holding the sample container in advance prior to transfer to said holder, said tray having a plurality of holding cavities spaced apart at uniform intervals; auto-sampler means disposed and operable for conveying the sample container between said tray and said holder and back to said tray, said auto-sampler having gripper means for grasping and releasing the sample container; and means for moving said oven between an analysis position in which said oven encloses said sample holder and the sample container held by said sample holder, and a container transfer position in which said oven is spaced from said holder to permit said auto-sampler means to convey the sample container between said tray and said sample holder; whereby the sample container is fed and discharged between said tray and said holder so that thermogravimetry may be accomplished on successive samples.

2. Apparatus as defined in claim 1 wherein said auto-sampler means comprises: a first robot mechanism carrying said gripper means and operative for moving said gripper means between a sample container gripping state and a sample container releasing state; and a second robot mechanism coupled to said first robot mechanism and operative for moving said gripper means between a first position above said tray and a second position above said holder.

3. Apparatus as defined in claim 2 wherein said second robot mechanism is further operative for moving said gripper means vertically.

4. Apparatus as defined in claim 3 wherein said second robot mechanism is operative such that movement of said gripper means between said first and second positions includes a pivotal movement about a vertical axis and a horizontal translational movement in a radial direction relative to the vertical axis.

5. Apparatus as defined in claim 4 wherein: said thermobalance comprises a balance beam supporting said holder for permitting vertical movement of said holder as a function of the weight of the sample in the sample container held by said holder; and said means for moving said oven move said oven vertically so that in said container transfer position said oven is spaced above said holder.

6. Apparatus as defined in claim 4 wherein said apparatus is a horizontal differential type thermogravimetric apparatus and further comprises a reference holder for holding a reference sample container containing a reference sample.

7. Apparatus as defined in claim 6 wherein said thermobalance comprises: a sample side balance beam supporting said sample holder for permitting vertical movement of said sample holder; and a reference side balance beam supporting said reference holder for permitting vertical movement of said reference holder and wherein said means for moving said oven move said oven horizontally so that in said container transfer position said oven is spaced horizontally from said holders.

8. Apparatus as defined in claim 7 wherein said apparatus further comprises tray displacement means connected for displacing said tray to bring a selected holding location into alignment with said gripper means.

9. Apparatus as defined in claim 1 wherein: said thermobalance comprises a balance beam supporting said holder for permitting vertical movement of said holder as a function of the weight of the sample in the sample container held by said holder; and said means for moving said oven move said oven vertically so that in said container transfer position said oven is spaced above said holder.

10. Apparatus as defined in claim 1 wherein said apparatus is a horizontal differential type thermogravimetric apparatus and further comprises a reference holder for holding a reference sample container containing a reference sample.

11. Apparatus as defined in claim 10 wherein said thermobalance comprises: a sample side balance beam supporting said sample holder for permitting vertical movement of said sample holder; and a reference side balance beam supporting said reference holder for permitting vertical movement of said reference holder and wherein said means for moving said oven move said oven horizontally so that in said container transfer position said oven is spaced horizontally from said holders.

12. Apparatus as defined in claim 1 wherein said apparatus further comprises tray displacement means connected for displacing said tray to bring a selected holding location into alignment with said gripper means.

* * * * *